United States Patent [19]

Tiep et al.

[11] Patent Number: 4,612,928
[45] Date of Patent: Sep. 23, 1986

[54] METHOD AND APPARATUS FOR SUPPLYING A GAS TO A BODY

[76] Inventors: Brian L. Tiep, 632 Norumbega Dr., Monrovia, Calif. 91016; Robert E. Phillips, 12217 Iredell St., Studio City, Calif. 91601; Ben A. Otsap, 7661 Airport Blvd., Los Angeles, Calif. 90045

[21] Appl. No.: 645,050

[22] Filed: Aug. 28, 1984

[51] Int. Cl.$^4$ .............................................. A61M 16/00
[52] U.S. Cl. ............................ 128/204.23; 128/207.18
[58] Field of Search ..................... 128/203.13, 203.18, 128/203.22, 203.12, 204.21, 204.23, 204.26

[56] References Cited

U.S. PATENT DOCUMENTS

| | | | |
|---|---|---|---|
| 3,736,949 | 6/1973 | Wolter et al. | 128/204.24 |
| 3,768,468 | 10/1973 | Cox | 128/204.21 |
| 3,910,270 | 10/1975 | Stewart | 128/204.24 |
| 3,976,065 | 8/1976 | Durkan | 128/204.24 |
| 4,054,133 | 10/1977 | Myers | 128/204.26 |
| 4,163,450 | 8/1979 | Kirk et al. | 128/204.23 |
| 4,323,064 | 4/1982 | Hoenig et al. | 128/204.21 |
| 4,381,002 | 4/1983 | Mon | 128/204.24 |
| 4,457,303 | 7/1984 | Durkan | 128/204.24 |

OTHER PUBLICATIONS

Auerbach et al., "A New Oxygen Cannula System Using Intermittent-Demand Nasal Flow", Chest, vol. 74, pp. 39–44, Jul. 1978.

Primary Examiner—Henry J. Recla
Attorney, Agent, or Firm—Edward D. O'Brian; K. H. Boswell

[57] ABSTRACT

An apparatus which minimizes the amount of oxygen needed to maintain a specific oxygen level in the blood of an individual can be constructed so as to use a transducer and other circuit components to obtain a first series of pulses or signals corresponding to the individual's breathing. A divider or counter processes the signals or pulses of the first series to create a second series of pulses or signals corresponding to periodic pulses or signals of the first series. The pulses or signals of the second series are used to periodically open a valve to deliver oxygen to the individual at about the start of the person's periodic breathing cycles.

12 Claims, 1 Drawing Figure

U.S. Patent    Sep. 23, 1986    4,612,928
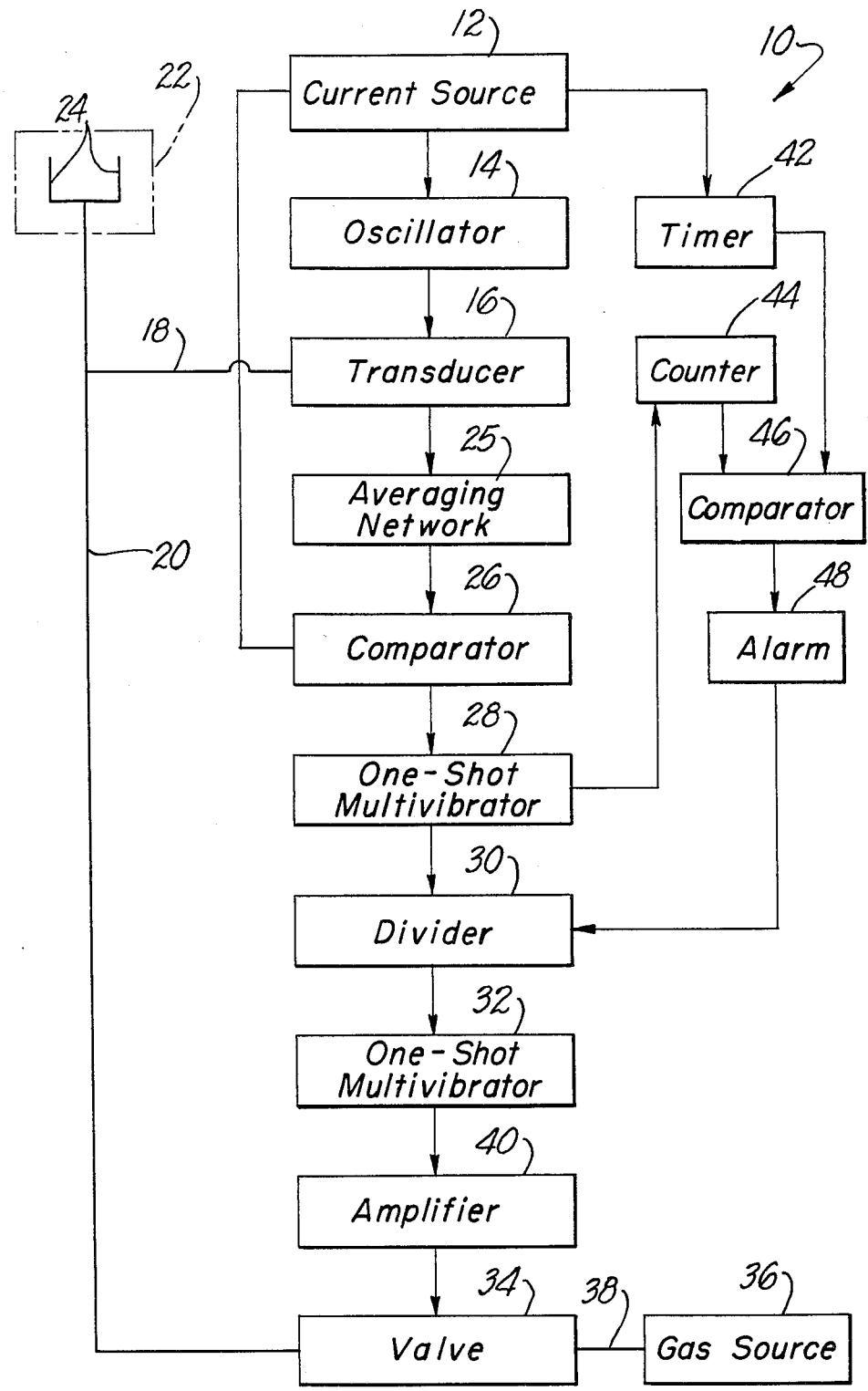

METHOD AND APPARATUS FOR SUPPLYING A GAS TO A BODY

BACKGROUND OF THE INVENTION

The invention set forth in this specification pertains to the delivery of a gas to the pulmonary tract of a living body. This invention is considered to be of particular significance in connection with the delivery of oxygen to a human being as, for example, during oxygen therapy.

In the past it has been quite common to deliver oxygen to a person needing such therapy by enclosing the area around the nose and the mouth of the individual with a so-called "tent" and supplying oxygen to the interior of the tent so that the person will tend to inhale an oxygen enriched gas from the interior of the tent. It is also common to administer oxygen by either conveying pure oxygen or an oxygen enriched air mixture directly to the nostrils of such a person through small tubes commonly referred to as nasal cannula. At times the structure consisting of two of such tubes joined together in one manner or another is referred to as a nasal cannula structure.

It has been determined that these widely used procedures for delivering oxygen to the pulmonary tract of an individual needing oxygen therapy are comparatively wasteful of oxygen. As a consequence of this a number of efforts have been made to develop oxygen delivery structures which operate in such a manner as to use less oxygen than required by prior therapy methods in order to maintain a specific desired oxygen level within the blood of an individual. A number of different devices have been developed for this purpose. In general it may be considered that all of such prior devices for this purpose have employed one or more internal structures to regulate or tend to regulate the flow of oxygen to the patient in accordance with the patient's breathing cycle. These prior gas delivery procedures which are related to the breathing cycle have been directed towards modulating the flow of oxygen or oxygen enriched gas so that such gas does not escape or does not significantly escape to the ambient air before it is inhaled.

It will be recognized that such apparatuses which are designed to regulate the flow of such gas such as oxygen can be quite beneficial and desirable. However, it is considered that these prior devices are wasteful of oxygen inasmuch as they relate to the delivery of oxygen to the pulmonary tract of the body to successive breathing cycles. While under some conditions this may be quite desirable there are conditions where this is somewhat undesirable because it results in the extravagant utilization of oxygen without the achievement of a maximum of benefit in maintaining the oxygen level of the blood.

BRIEF SUMMARY OF THE INVENTION

It will be apparent from the preceding that there is a need for a new and improved procedure for the delivery of a gas such as oxygen to the pulmonary tract of the body. More specifically there is a need to deliver such gas in such a manner as to minimize the amount of gas required to obtain a specific level of benefit. Perhaps it is best to illustrate this. In the normal utilization of the present invention the intent is to minimize the amount of oxygen which has to be supplied to an individual in order to maintain a specific oxygen content in the blood.

The invention is intended to fullfil the need indicated in this discussion. It is intended to provide both a new and improved method and a new and improved apparatus for delivering a gas to the pulmonary tract of a living body. It is intended to provide a method as indicated which can be easily and conveniently carried out and which can be used to obtain an economically desirable saving in oxygen. The invention is intended to provide apparatus for use in delivering a gas to the pulmonary tract of the body which may be easily and conveniently constructed at a comparatively nominal cost, which will operate satisfactorily over a long period and which requires little or no maintenance as a result of normal utilization.

It is not to be assumed from this that these are the only objectives of the present invention. In the interest of brevity no effort is made herein to delineate all the possible objectives or advantages of this invention. It is believed that such further objectives and advantages will be apparent to those skilled in the design and construction of oxygen therapy apparatus from a detailed consideration in the remainder of this specification.

Those aspects of the present invention pertaining to a process are achieved by providing a process of delivering a gas to an entrance into the pulmonary tract of a body during breathing in which the gas is placed in a location where it will be inhaled during the inhalation part of the breathing cycle in which the improvement comprises: obtaining a first series of repetitive electric signals corresponding to the breathing rate of the body: processing said first series of signals so as to obtain a second series of repetitive signals, and said first series of signals being a rate which is a multiple of no less than one of the rate of said second series, and using said signals of said second series to cause release of said gas at about the start of the inhalation portion of the breathing cycle to said location so that the released gas will be inhaled at about the start of the inhalation part of the breathing cycle.

Those aspects of the present invention which pertain to an apparatus are achieved by providing an apparatus for delivering a gas to an entrance into the pulmonary tract of a body during breathing, said apparatus having a delivery means for conveying said gas from the source of said gas to said entrance in which the improvement comprises: transducer means responsive to the movement of gas relative to said entrance so as to provide a first series of signals corresponding to the breathing rate of said body, said transducer means being adapted to be located so as to be actuated by the breath during at least said part of the breathing cycle, counter means for providing a second series of repetitive signals, said first series of signals being at a rate which is a multiple of not less than one of the rate of said second series, and actuating means for providing a series of signals corresponding to said signals of said second series which is of a predetermined duration connected to such counter means and valve means connected to said actuating means, said, valve means being located in said means for conveying said gas to said transducer means, said actuating means and said valve means being coordinated so that said valve means is open only at intervals corresponding in duration to the signals provided by said actuating means which are timed so that the said gas is available to be inhaled at said entrance of said respiratory tract at about the start of inhalation when there is a signal from said second series.

BRIEF DESCRIPTION OF THE DRAWINGS

Because of the nature of the invention and because of the inherent limitations of a summary it is considered that an understanding of the present invention requires a discussion which is much more involved then the preceding summary. This discussion is best predicated on a consideration of the accompanying drawing in which:

The FIGURE is a block diagram illustrating the nature of a presently preferred form of an apparatus in accordance with this invention.

The accompanying block diagram is primarily intended to illustrate for explanatory purposes the nature of a presently preferred apparatus in accordance with this invention. An actual apparatus in accordance with this invention will be constructed so as to utilize the concepts and principles of the invention summarized in the appended claims. From a consideration of the remainder of this specification and these claims it will be realized that other apparatus then that shown can be constructed through the use of routine skill in the pulmonary medical electronics fields.

DETAILED DESCRIPTION

The apparatus 10 will normally include an appropriate conventional current source 12. Preferrably, but not necessarily this source 12 is capable of providing a standard or uniform output voltage. In a comparatively small apparatus 10 which can be easily carried from one location to another this current source 12 may be only a battery or may include a battery and a voltage regulator. In other applications as, for example, in hospitals, line current may be directly utilized in an established or conventional manner as the source 12. A conventional on-off switch has not been shown in connection with the current source 12 because the utilization of such a switch is so self apparent.

The current source 12 is used to provide an output voltage to a conventional oscillator 14 capable of providing an output consisting of a series of repetitive pulses of a uniform amplitude at a uniform rate. The output from this oscillator 14 is provided to a transducer 16 as shown. This transducer 16 is extremely important to the invention. In the complete apparatus 10 the transducer 16 is connected to a lateral line 18 leading off of a principle supply line 20 used to supply oxygen to a nasal cannula structure 22.

This cannula structure 22 will normally be of a conventional design and will include two separate prongs 24 which are adapted to be inserted into the nostrils (not shown) of a user of the apparatus 10. If desired these prongs 24 may be referred to as individual cannula or tubes. It is to be emphasized that the present invention does not reside in the cannula structure 22 per se. If desired various equivalants may be substituted for this nasal cannula structure 22. Thus, for example, in some circumstances it may be necessary or desirable to substitute a distribution tube or housing located immediately adjacent to the nostrils of the user for it.

The transducer 16 employed may be of any conventional or known type which will provide a signal or a change in a signal or pulses or change in pulses in response to a pressure change corresponding to that capable of being caused in the line 18 by a user of the apparatus 10. In the presently preferred manner of practicing this invention the transducer 16 is a type of variable capacitor which will vary the amplitude of the pulses from the oscillator 14 in accordance with the breathing cycle of a user of this apparatus 10. Throughout the breathing cycle the pulses produced by transducer 16 of varying amptitude may be referred to as a first series of signals or pulses corresponding to the breathing pattern or cycle of a user of the apparatus 10.

In this apparatus 10 this first series of pulses of varying amplitude from transducer 16 is passed to what is referred to herein as an averaging network 25. This network 25 is a known type of integrating circuit which processes the pulses of varying amplitude from the transducer 16 so as to achieve a continuously varying voltage. In the preferred manner of practicing this invention this voltage will increase during the portion of the breathing cycle when the individual using the apparatus 10 ceases exhalation and commences inhalation.

This signal having a continuously varying voltage obtained from the averaging network 25 is passed to a conventional type of comparator 26. Normally this comparator 26 will be an operational amplifier. It is to be understood, however, that other similar types of devices may be employed as the comparator 26. In this comparator 26 the voltage provided by the averaging network 25 is compared with a reference voltage supplied as shown from the current source 12.

When the voltage of the signal from the network 25 exceeds a threshold value corresponding to the voltage at about the start of inhalation the comparator 26 will provide a signal to a one shot multi-vibrator 28. In essence it can be considered that the averaging network 25 and the comparator 26 more or less "refine" the signals or pulses produced by the transducer 16 so that the comparator 26 provides a first series of signals which not only directly corresponds directly to the breathing pattern of a user of the apparatus 10 but which specifically corresponds to the start of the inhalation cycle.

The purpose of this multivibrator 28 is to again "refine" the first series of signals into a series of pulses of a definite duration. The need for this is best explained in connection with the components described in the preceding. With these components the comparator 26 provides a series of individual pulses of a comparatively limited width or duration. The duration of these pulses is made uniform by the one shot multi-vibrator 28.

Further, the duration of the pulses from the one shot multivibrator 28 will preferably be set so as to be sufficiently long as to effectively minimize any chance of an extraneous pulse resulting from the operation of transducer 16 being inserted within the what is referred to herein as a first series of signals or pulses. Normally the pulse width of the pulses from the one shot multivibrator 28 will be of about ½ second duration. Because of its function this one shot multivibrator 28 may be referred to as a type of lock out device or means which tends to lock out or prevent extraneous pulses or signals from operating various components as are subsequently described.

This is important because of the operation of a divider or counter 30 used in this apparatus 10. This divider or counter 30 receives the first series of pulses from the multivibrator 28 and processes this first series of pulses so as to provide a second series of pulses corresponding to periodic of the pulses of the first series. In other words the divider 30 will provide a second series of pulses corresponding to every first, second, third, fourth, or other pulse of the first series of pulses depending upon how the divider 30 is constructed or adjusted at any particular time.

It is preferably constructed so that it can be adjusted so that the rate of the pulses in the first series will be a multiple of no less than one of the rate of the pulses of the second series. It will be apparent from this that the rate of the pulses in the first and the second series can be the same although normally this will not be the case.

The second series of pulses from the divider or counter 30 is supplied to a second one shot multivibrator 32. This multivibrator 32 is intended to convert the pulses of the second series into pulses of a predetermined duration to the cannula structure 24. This duration preferably corresponds to the time interval when it is desired to open an electrically operated valve 34 in order to allow oxygen to pass from a conventional supply 36 through a line 38 and the valve 34 into the line 20.

It is presently considered preferable to use a known type of electrically operated valve as the valve 34. The supply 36 can be of any conventional type. Normally it will be a small tank (not separately shown). The time duration of the pulses from the multivibrator 32 may be varied so as to accomodate for the varying oxygen demands of different persons utilizing the apparatus 10. It can also be constructed so that these pulses can be varied to compensate for variation in the pressure of the oxygen delivered for the supply 36 or any other variation which might vary the flow of oxygen to the cannula structure 24.

Normally it is preferable to establish a wide pulse width for the multivibrator 32 which need not be changed as the apparatus 10 is used with a standard source of oxygen. Thus, for example, when an oxygen supply is either a tank or a line which is regulated so as to supply oxygen at a pressure of 20 to 24 psi normally it will be satisfactory if the pulse widths of the pulses of second series of pulses from the one shot vibrator 32 will be about 200 milliseconds. Other periods such as periods of about 150 to about 400 milliseconds are usually acceptable. Normally it will be necessary to use a conventional amplifier 40 in order to amplify the signals of the second series in order to operate the valve 34.

From this discussion it will be apparent that the amount of oxygen delivered to a patient may be varied in several ways. one of these is by varying the pressure of oxygen or other gas from the supply 36. Another is by varying the duration of the pulses of the second series from the multivibrator 32. A third is by adjusting the counter or divider 30 so as to increase the ratio of the number of pulses of the second series to the number of pulses of the first series. When the apparatus 10 is used with a supply of gas at a standardized pressure and is otherwise constructed or adjusted for use with an average person it will not usually be desirable to vary the amount of oxygen delivered.

It is believed that the operation of the apparatus 10 will be essentially self apparent from the preceding discussion. When the cannula structure 22 is in place the current source 12 is turned on and oxygen is supplied from the source 36. As the apparatus 10 to is used it will operate as previously indicated. This will result in oxygen or another gas being supplied to line 20 at about the start of each of the periodic of the breathing cycles of the user of the apparatus 10. These will not usually be successive cycles. These periodic cycles will correspond to the pulses of the second series.

Thus, for example, when the apparatus 10 is employed to administer oxygen the oxygen can be administered through the tube 20 at about the start of every second, third, or fourth breath depending upon how the divider 30 is constructed or adjusted. This oxygen which passes the valve 34 each time it is opened will displace other oxygen from within the line 20 to the cannula 24 where it will be placed at or about the entrance into the pulmonary tract at about the start of the breathing cycle. Because the oxygen is "applied" or "used" at this point it will be effectively utilized by a body in maintaining the oxygen level of the blood.

It will be apparent for a consideration of the preceding that there will be an increase in the pressure within the lines 18 and 20 each time the valve 34 is opened. Each such increase will, of course, be detected by the transducer 16 in the same manner in which the transducer 16 detects a pressure change during the breathing cycle. The pressure change caused by the operation of the valve 34 will come closely after the pressure change from breathing detected of the transducer 16 at about the start of each inhalation cycle. As a consequence of this the pressure changes resulting in the release of gas will come during the pulses from the multivibrator 28. As previously indicated the pulses from this multivibrator 28 are of sufficient duration so that change in pressure resulting from the release of oxygen or other gas will not alter the pulses or signals or what are described herein as the first series of pulses or signals.

If desired the apparatus 10 can be modified so as to be capable of supplying more oxygen then would be supplied then indicated in the preceding in case the breathing rate of an individual should increase significantly as a result of physical activity or the like. The apparatus 10 maybe converted into such an "adaptive" apparatus by the use of a timer 42 and another counter 44. This timer 42 is preferably powered by the current source 12. The counter 44 is intended to count individual pulses in the first series of pulses as obtained from the multivibrator 28. A known type of rate determination circuit or comparator 46 receives the outputs from the timer 42 and the counter 44 so as to determine if there is any significant change in the rate of breathing of the user of the apparatus 10. Preferably a known type of alarm 48 is connected to the rate determination circuit 46 so as to provide an audible or similar alert in the event the breathing rate exceeds an undesired value.

If there is a significant change in this rate in the comparator 46 will provide a signal to the divider 30 so as to adjust the divider 30 to increase the number of pulses of the second series of pulses per pulse of the first series when the breathing rate is going up or decrease the number of pulses of the second series of pulses per pulse of the first series when the breathing rate is being decreased. The precise amount of change in the breathing rate necessary to effect a specific change in the pulse rate of the second series of pulses is considered to be a matter which is best left to the judgement of a medical practioner.

We claim:
1. A process of delivering a gas to an entrance into the pulmonary tract of a patient during breathing in which the gas is placed in a location where it will be inhaled during the inhalation part of the breathing cycle in which the improvement comprises:
   obtaining a series of repetitive electric signals of varying amplitude from a series of uniform repetitive pulses, said signals of varying amplitude corre- sponding to the breathing rate of the patient, said series of signals of varying amplitude being obtained by using a variable capacitor transducer means capable of being activated by the spontaneous breathing of the patient where it can be so activated and using the spontaneous breathing of the patient to so activate said transducer means, the variations between said signals of varying amplitudes corresponding to various inhalation/exhalation intervals during the breathing cycle, selecting periodic signals of said series of signals of varying amplitude corresponding to inhalation intervals so as to create another series of signals, and using said signals of said other series to cause release of said gas at about the start of said inhalation portion of said breathing cycle to said location so that said released gas will be inhaled at about the start of said inhalation part of said breathing cycle.

2. An apparatus for delivering gas to an entrance into the pulmonary tract of a patient during breathing, said apparatus having a conveying means for conveying said gas from a source of said gas to said entrance in which the improvement comprises:

a current source providing a reference voltage, oscillator means for converting said voltage from said current source into a series of repetitive pulses of uniform amplitude and duration, a variable capacitor transducer means responsive to the movement of gas relative to said entrance so as to convert the pulses of said series of uniform repetitive pulses into a series of pulses of varying amplitude, the amplitudes which correspond to various inhalation/exhalation intervals during the breathing cycle, said transducer means being adapted to be located so as to be actuated by the spontaneous breathing of the patient, counter means for providing a series of repetitive signals from said series of pulses of varying amplitude, said signals provided by said counter means being provided at a rate which is a multiple of not less than one of the rate at which said series of uniform amplitude pulses are provided, and actuating means for providing a series of signals of a predetermined duration corresponding to said signals of said series of repetitive signals connected to said counter means, and valve means connected to said actuating means, said valve means being located in said means for conveying said gas to said transducer means, and said actuating means and said valve means being coordinated so that said valve means is open only at intervals corresponding in duration to the signals provided by said actuating means, which intervals are timed so that the said gas is available to be inhaled at said entrance to said respiratory tract at about the start of inhalation when there is a signal from said second series.

3. An apparatus as claimed in claim 2 including: lock out means for preventing the extraneous signals from altering said signals of said first series of signals of varying amplitude.

4. An apparatus as claimed in claim 2 including: rate determining means for determining a change in the breathing rate of the body, said rate determining means being connected to said counter means so as to increase the number of pulses of varying amplitude when the breathing rate is increasing and to decrease the number of pulses of varying amplitude when the breathing rate is decreasing.

5. An apparatus as claimed in claim 2 including: lock out means for preventing extraneous signals from altering said signals of said first series of signals of varying amplitude, rate determining means for determining a change in the breathing rate of the body, said rate determining means being connected to said counter means so as to increase the number of pulses of varying amplitude when the breathing rate is increasing and to decrease the number of pulses of varying amplitude when the breathing rate is decreasing.

6. An apparatus as claimed in claim 2 wherein:

said conveying means comprises a line leading from said source of said gas and a nasal cannula structure connected to said line, said transducer means is connected to said line extending between said source of said gas and said nasal cannula structure.

7. An apparatus for delivering gas to an entrance into the pulmonary tract of a patient during breathing, said apparatus having a conveying means for conveying said gas from the source of said gas to said entrance in which the improvement comprises:

a current source providing a predetermined reference voltage corresponding to about the start of an inhalation, oscillator means for converting said voltage from said current source into a series of repetitive pulses of uniform amplitude and duration, transducer means responsive to the movement of gas relative to said entrance so as to provide a first series of signals corresponding to the breathing rate of said patient, said transducer means being adapted to be located so as to be actuated by the spontaneous breathing of the patient during at least said part of the breathing cycle, said transducer means is a capacitor capable of converting the pulses from said oscillator means into pulses of varying amplitude, the amplitudes of said pulses corresponding to various inhalation/exhalation intervals during the breathing cycle, and comparator means for comparing the output of said transducer means and said reference voltage so as to provide a first series of signals corresponding to about the start of inhalation, counter means for providing a second series of repetitive signals from said first series of signals provided by said comparator means, said first series of signals being at a rate which is a multiple of not less than one of the rate of said second series, and actuating means for providing a third series of signals of a predetermined duration corresponding to said signals of said second series connected to said counter means, and valve means connected to said actuating means, said valve means being located in said means for conveying said gas to said transducer means, and said actuating means and said valve means being constructed so that said valve means is open only at intervals corresponding in duration to the signals provided by said actuating means which are times so that the said gas is available to be inhaled at said entrance of said respiratory tract at about the start of inhalation when there is a signal from said second series, said conveying means comprises a line leading from said source of said gas and a nasal cannula structure connected to said line, said transducer means is connected to said line extending between said source of said gas and said nasal cannula structure.

8. An apparatus as claimed in claim 7 including:

lock out means for preventing extraneous pulses from altering said signals of said first series of signals.

9. An apparatus as claimed in claim 8 wherein:

said lock out means is a one shot multivibrator.

10. An apparatus for delivering gas to an entrance into the pulmonary tract of a patient during breathing, said apparatus having a conveying means for conveying said gas from the source of said gas to said entrance in which the improvement comprises:

a current source providing a predetermined reference voltage corresponding to about the start of an inhalation, oscillator means for converting sad voltage from said current source into a series of repetitive pulses of uniform amplitude and duration, transducer means responsive to the movement of gas relative to said entrance so as to provide a series of pulses corresponding to the breathing rate of said patient, said transducer means being adapted to be located so as to be actuated by the spontaneous breathing of the patient during at least part of the breathing cycle, said transducer means is a capacitor capable of converting the pulses from said oscillator means into pulses of varying amplitude, the amplitudes of said pulses corresponding to various inhalation/exhalation intervals during the breathing cycle, and comparator means for comparing the output of said transducer means and said reference voltage so as to provide a first series of signals corresponding to about the start of inhalation, counter means for providing a second series of repetitive signals from said first series of signals provided by said comparator means, said first series of signals being at a rate which is a multiple of not less than one of the rate of said second series, and actuating means connected to said comparator means for providing a third series of signals of a predetermined duration corresponding to said signals of said second series, and valve means connected to said actuating means, said valve means being located in said means for conveying said gas to said transducer means, and said actuating means and said valve means being constructed so that said valve means is open only at intervals corresponding in duration to the signals provided by said actuating means which are timed so that said gas is available to be inhaled at said entrance of said respiratory tract at about the start of inhalation when there is a signal from said second series.

11. An apparatus for delivering gas to an entrance into the pulmonary tract of a patient during breathing, said apparatus having a converying means for conveying said gas from the source of said gas to said entrance in which the improvement comprises:

a current source providing a predetermined reference voltage corresponding to about the start of an inhalation, oscillator means for converting said voltage from said current source into a series of repetitive pulses of uniform amplitude and duration, transducer means responsive to the movement of gas relative to said entrance so as to provide a series of pulses corresponding to the breathing rate of said patient, said transducer means being adapted to be located so as to be actuated by the spontaneous breathing of the patient during at least part of the breathing cycle, said transducer means is a capacitor capable of converting the pulses from said oscillator means into pulses of varying amplitude, the amplitudes of said pulses corresponding to various inhalation/exhalation intervals during the breathing cycle, and comparator means for comparing the output of said transducer means and said reference voltage so as to provide a first series of signals corresponding to about the start of inhalation, actuating means connected to said comparator means for providing a second series of signals of a predetermined duration corresponding to said first series of signals provided by said comparator means, and valve means connected to said actuating means, said valve means being located in said means for conveying said gas to said transducer means, and said actuating means and said valve means being constructed so that said valve means is open only at intervals corresponding in duration to the second series of signals provided by said actuating means which are timed so that said gas is available to be inhaled at said entrance of said respiratory tract at about the start of inhalation when there is a signal from said second series.

12. A process of delivering a gas to an entrance into the pulmonary tract of a body of a person during breathing in which the gas is placed in a location where it will be inhaled during the inhalation part of the breathing cycle in which the improvement comprises:

generating a series of uniform pulses, locating a variable capacitor serving as a transducer means which is capable of being activated by the spontaneous breathing of said person where it can be so activated, using the spontaneous breathing to vary the capacitance of said capacitor by using the varying capacitance of said capacitor to change said series of uniform pulses into a series of varying pulses corresponding to the breathing of said person, changing said series of varying pulses into a series of pulses of uniform duration, selecting periodic pulses of said series of pulses of uniform duration corresponding to inhalation and, using said selected pulses to control the operation of a valve to cause the release of said gas at about the start of said inhalation part of the breathing cycle to said location so that said released gas will be inhaled at about the start of said inhalation part of said breathing cycle.

* * * * *